(12) United States Patent
Martin et al.

(10) Patent No.: US 6,345,737 B1
(45) Date of Patent: Feb. 12, 2002

(54) DEVICE FOR DISPENSING A SINGLE DOSE OF FLUID

(75) Inventors: Claude-Georges Martin, Yville; Ludovic Petit, Vitot, both of (FR)

(73) Assignee: Valois S.A., Le Neubourg (FR)

( * ) Notice: Subject to any disclaimer, the term of this patent is extended or adjusted under 35 U.S.C. 154(b) by 360 days.

(21) Appl. No.: 09/155,574

(22) PCT Filed: Apr. 1, 1997

(86) PCT No.: PCT/FR97/00575

§ 371 Date: Mar. 15, 1999

§ 102(e) Date: Mar. 15, 1999

(87) PCT Pub. No.: WO97/36691

PCT Pub. Date: Oct. 9, 1997

(30) Foreign Application Priority Data

Apr. 2, 1996 (FR) .............................................. 96/04119

(51) Int. Cl.$^7$ ................................................ B65D 88/54

(52) U.S. Cl. ........................................ 222/320; 222/162

(58) Field of Search ................................. 222/320, 321, 222/386, 162, 494

(56) References Cited

U.S. PATENT DOCUMENTS

| 4,344,744 A | * | 8/1982 | Schuster et al. ............. 222/321 |
| 4,921,142 A | * | 5/1990 | Graf et al. ................... 222/320 |
| 5,085,350 A | * | 2/1992 | Sugita ......................... 222/386 |
| 5,368,201 A | * | 11/1994 | Fuchs .......................... 222/320 |
| 5,370,318 A | * | 12/1994 | Weston ........................ 222/494 |
| 5,511,698 A | * | 4/1996 | Solignac ...................... 222/162 |

* cited by examiner

*Primary Examiner*—Kevin Shaver
*Assistant Examiner*—Thach H. Bui
(74) *Attorney, Agent, or Firm*—Sughrue Mion, PLLC

(57) ABSTRACT

A dispenser device for dispensing a single dose of liquid, the device comprising: a cylinder (4) containing said dose of liquid; a piston (10) which slides in sealed manner in said cylinder (4) between a storage position in which it isolates said cylinder and an actuated position; a piston actuator member (3); and an outlet passage (5) for connecting said cylinder (4) to an outlet orifice (6); the device being characterized in that said piston (10) includes a through-passage (11) which is closed in sealed manner in the storage position of the piston (10) by a closure member (20), said closure member being designed to open said through-passage (11) under the effect of a predetermined pressure which is created inside the cylinder (4), so as to enable said dose of liquid to be expelled through said through-passage (11).

9 Claims, 5 Drawing Sheets

DEVICE FOR DISPENSING A SINGLE DOSE OF FLUID

BACKGROUND OF THE INVENTION

The present invention relates to a dispenser device for dispensing a predetermined dose of liquid. More particularly, the invention relates to a device which contains a single dose of liquid, and which is discardable after said dose has been emitted. The liquid to be delivered may be a medicine, a cosmetic, or the like. The device of the invention is designed, in particular, for nose sprays, but could be used for other purposes, such as for ear sprays, mouth sprays, etc.

Such devices are known in the prior art. For example, document EP-A-0 311 863 describes a device including a cylinder of liquid in which a piston slides, the piston being secured to an actuating pushbutton. The device further includes an outlet passage which communicates with the cylinder of liquid. However, the outlet passage is not airtight and the liquid contained in the cylinder can become oxidized or polluted during storage on coming into contact with the air.

To solve that problem, document WO 93/00172 provides a movable piston in the cylinder, so that in the storage position, it cuts off communication between the outlet passage and the cylinder, and in the actuated position, it puts said outlet passage into communication with said cylinder, said piston being blocked in its storage position, and being displaced towards its actuated position in order to free the outlet passage, only if sufficient pressure appears in the cylinder to unblock it. However, that implementation, which operates in satisfactory manner, presents a certain number of drawbacks. Thus, in order to be able to determine in advance the level of pressure that is sufficient to unblock the piston, the dimensions of the piston must be very accurate to ensure effective blocking in the storage position, and guaranteed freeing when the device is actuated. This can turn out to be relatively difficult because of the dimensional tolerances that appear during manufacture of the various components parts of the device. Furthermore, manufacture and assembly of the piston itself are relatively complicated and therefore costly, thereby substantially increasing the cost of the device, particularly when the device is discardable after a single actuation. In addition, the presence of said piston, which is a movable element relative to all the other component parts of the device, represents a complication and therefore an undesirable increase in the cost of manufacturing and assembling the device.

Document WO 91/13281 describes a device including the characteristics mentioned in the preamble of claim 1.

An object of the present invention is to make a device of the above-mentioned type which does not have the above-mentioned drawbacks. In particular, the object of the present invention is to provide such a device which is simple and cheap to manufacture and assemble. This is particularly advantageous for devices which are discarded after a single actuation. Another object of the present invention is to provide such a device which guarantees total sealing during storage, and guarantees that the dose of liquid is dispensed in full when the device is actuated. Another object of the present invention is to provide such a device in which empty space is minimized. Another object of the present invention is to provide such a device which includes a minimum of independently movable parts.

The present invention therefore provides a dispenser device for dispensing a single dose of liquid, said device comprising a cylinder containing said dose of liquid, a piston which slides in sealed manner in said cylinder between a storage position in which it isolates said cylinder and an actuated position, a piston actuator member, an outlet passage for connecting said cylinder to an outlet orifice, and a spray nozzle which is disposed in the outlet passage for spraying the dose of liquid, said piston including a through-passage which is closed in sealed manner in the storage position of the piston by a closure member, said closure member being designed to open said through-passage under the effect of a predetermined pressure which is created inside the cylinder, so as to enable said dose of liquid to be expelled through said through-passage, the device being characterized in that said closure member is secured to said spray nozzle, said spray nozzle being movable between an initial position corresponding to the closed position of the closure member, and a final position corresponding to the open position of the closure member.

Said closure member is preferably movable between a closed position, in which it is disposed in said through-passage, and an open position, in which it is expelled out from said through-passage.

Advantageously, said through-passage is at least partially cylindrical, and said closure member has outside dimensions that are greater than the cross section of said through-passage so that it is blocked in the closed position, said closure member being expelled out from said through-passage under the effect of said sufficient pressure which is created in the cylinder.

In a particular embodiment of the invention, said through-passage includes a cavity designed to receive said closure member in its closed position.

The walls which form the through-passage of the piston are preferably deformable under the effect of a pressure that is sufficient to enable said closure member to be expelled.

In particular, said closure member may be a ball-bearing.

The spray nozzle advantageously includes an end portion which extends into said cylinder when the spray nozzle is in its initial position, said end portion being designed to occupy, at least in part, the empty space created in the through-passage when the spray nozzle is in its final position.

Said cylinder is advantageously made of glass.

Said piston is preferably fixed relative to said actuator member and is displaced in the cylinder together with said actuator member.

Said through-passage advantageously includes a substantially cylindrical first portion and a substantially cylindrical second portion, the cross section of said second portion being greater than that of said first portion, said closure member having outside dimensions which are greater than said section of the first portion and which are less than said cross section of the second portion.

BRIEF DESCRIPTION OF THE DRAWINGS

Other characteristics and advantages of the present invention appear from the following description of the invention, given as a non-limiting example, and with reference to the accompanying drawings, in which.

Figure 3:
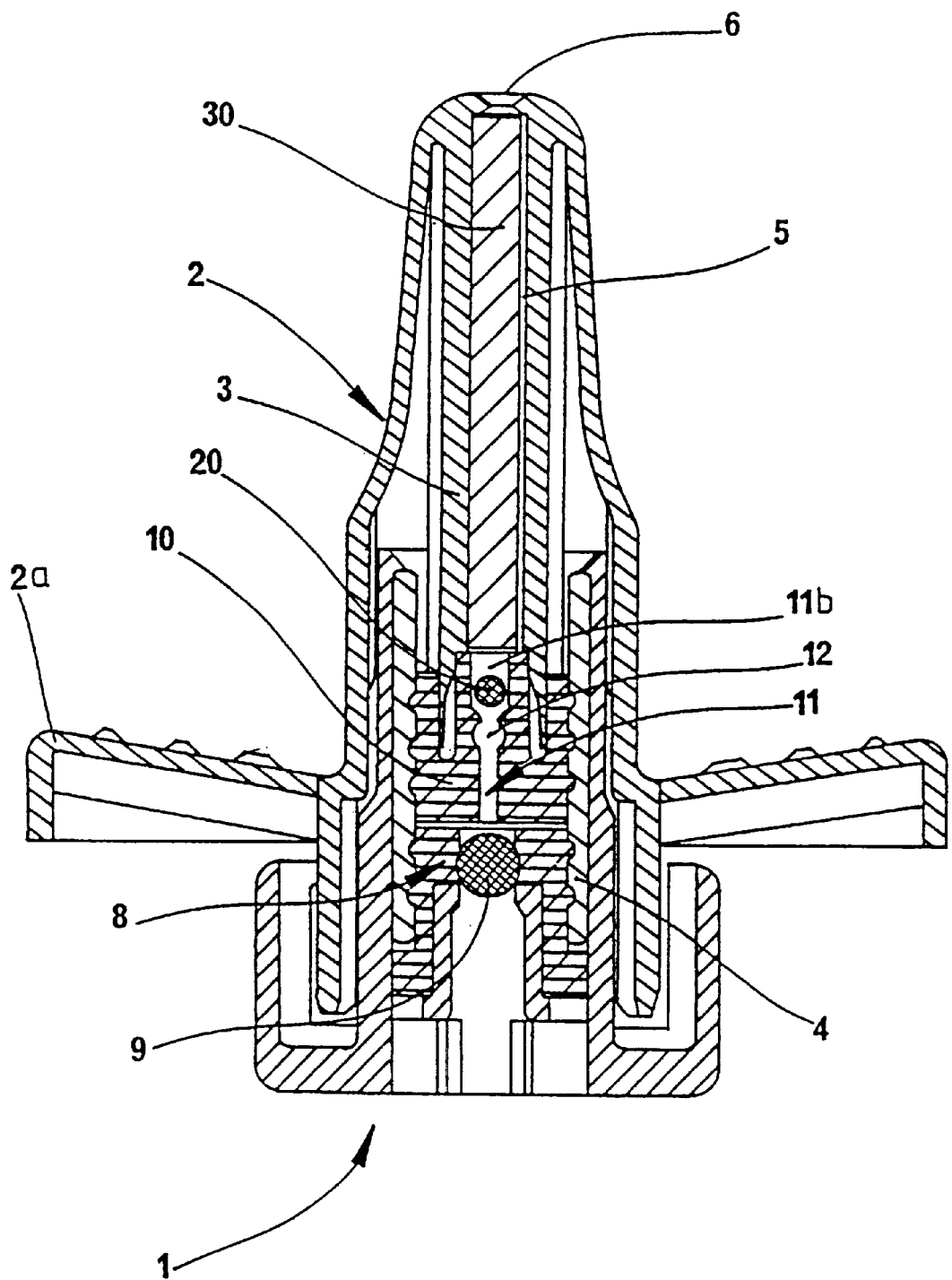
FIG. 3 is a view similar to that of FIG. 1, showing the device in its end-of-actuation position.
Figure 4:
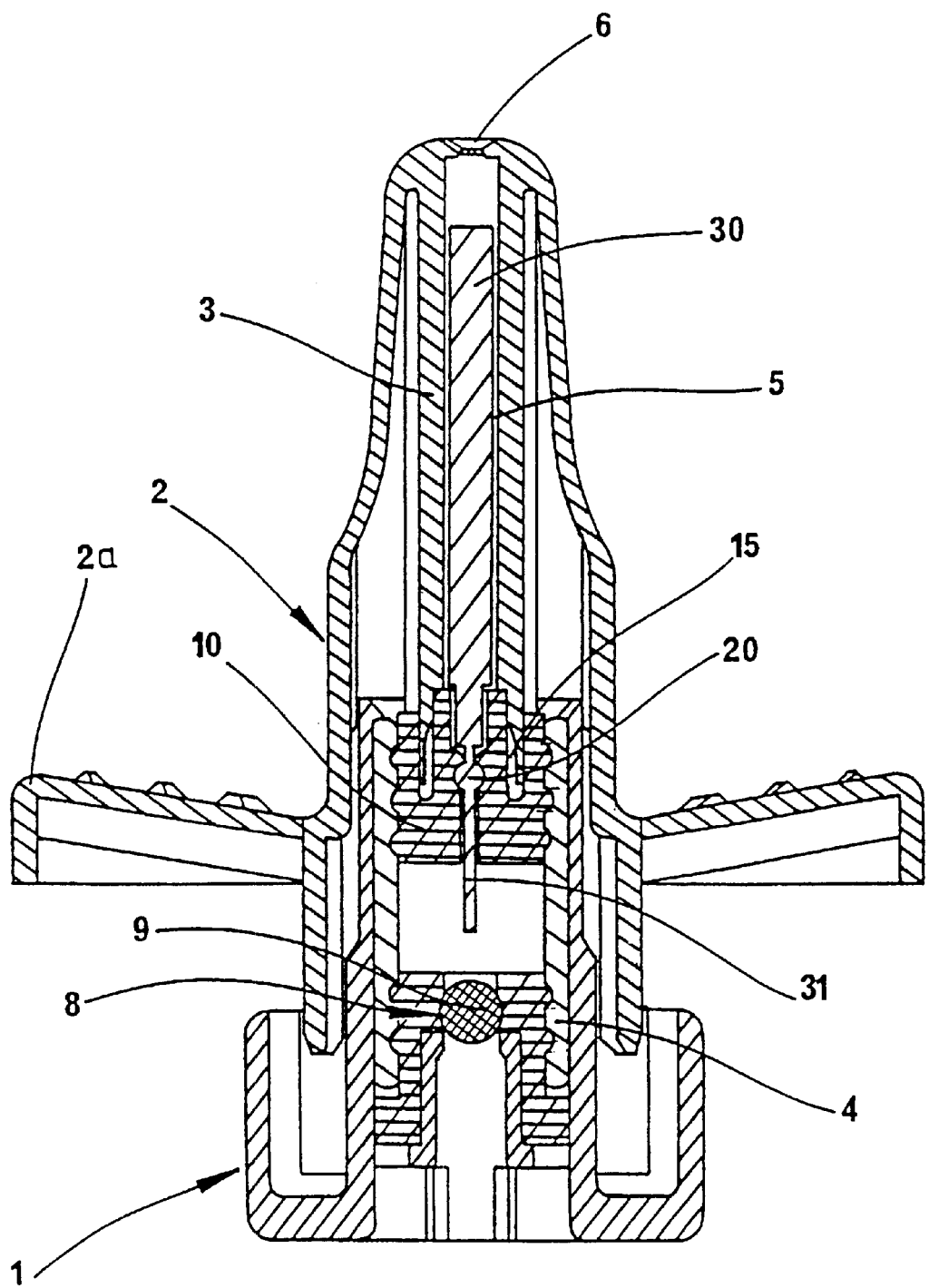
FIG. 4 is a view similar to that of FIG. 1, showing an embodiment of the device of the invention, in its storage position.
Figure 5:
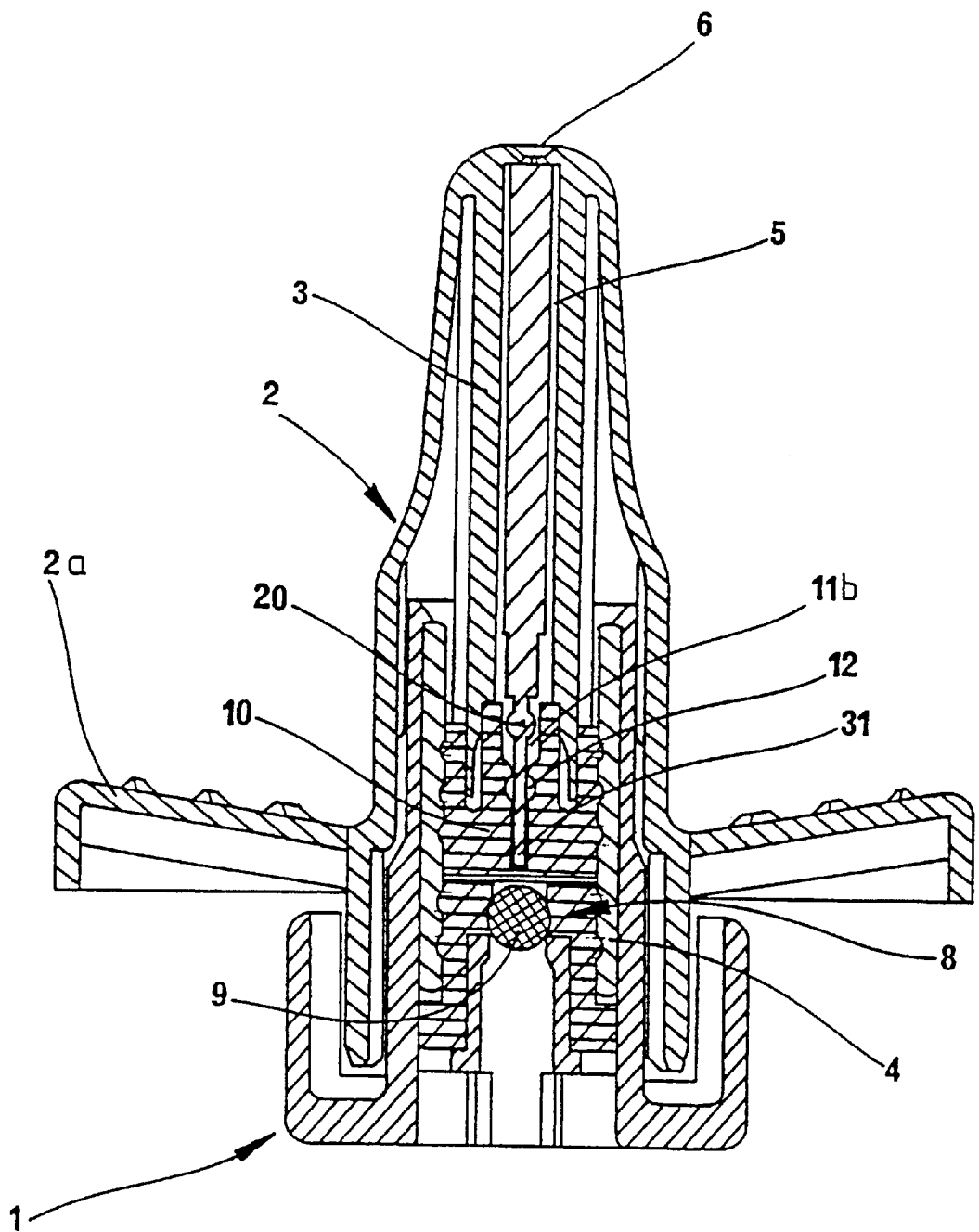
FIG. 5 is a view similar to that of FIG. 4, showing the device in its end-of-actuation position.

The dispenser device of the invention is shown in FIGS. 4 and 5. The embodiment of FIGS. 1 to 3 is not covered by the invention, but is described for explanatory purposes.

DESCRIPTION OF PREFERRED EMBODIMENTS

The dispenser device advantageously has an outside shape similar to the device described in document WO 93/00172. The device thus has two main portions which are movable relative to each other, comprising a first portion 1 slidable in a second portion 3. The first portion 1, which is the bottom portion when the device is in the position shown in the figures, includes a cylinder 4 which can advantageously be made in the form of a right circular tube fixed to said bottom portion 1. The cylinder 4 may possibly be an integral part of said bottom portion 1. However, for certain liquids, it is advantageous to make said cylinder 4 out of a material which is inert relative to the liquid, e.g. of glass. The cylinder 4 is closed at one end in completely sealed manner by a stopper 8. The stopper 8 is advantageously made of an elastomer material ensuring good sealing, and has a central channel enabling the cylinder to be filled with the liquid, said channel being closed, after filling, by a suitable element such as a ball-bearing 9. It is also possible, however, to provide a stopper 8 which does not include a filling channel, in which case, the cylinder can be filled with liquid by means of a filling needle which would pierce the elastomer material of the stopper 8 in order to fill the cylinder 4 with the liquid, a degassing needle being simultaneously provided to remove the air initially contained in said cylinder 4. In the figures, the end of the cylinder 4 which is closed by the stopper 8 is the bottom end. When the device is actuated, the bottom portion 1 of the device is designed to slide inside the top portion 2. The top portion 2 includes an actuator member 3, such as a rod, which is secured to the top portion 2, and which acts on a piston 10 which is slidably mounted inside the cylinder 4 on the end facing the stopper 8. The piston 10 is designed to be displaced inside the cylinder 4 between a storage position, shown in FIGS. 1, 2, and 4, in which it completely isolates the cylinder 4 from the outside, and an actuated position, shown in FIGS. 3 and 5, in which the liquid contained in the cylinder 4 has been dispensed by the dispenser device. To actuate the device, the top portion 2 advantageously includes actuation wings 2a which extend laterally on either side of the top portion 2, and on which a user presses the fingers to actuate the device, while maintaining the thumb on the bottom portion 1 so that the device can be actuated manually in very simple manner. As shown in FIGS. 1 and 2, the actuation wings 2a need only extend on either side of the device, as can be seen in FIG. 1, and need not surround the entire periphery of said top portion 2. The top portion 2 further includes an outlet passage 5 designed to connect the cylinder 4 to an outlet orifice 6. In addition, a spray nozzle 30 is advantageously disposed near to said orifice 6 to guarantee good spraying of the dose of liquid contained in the cylinder 4.

Figure 1:
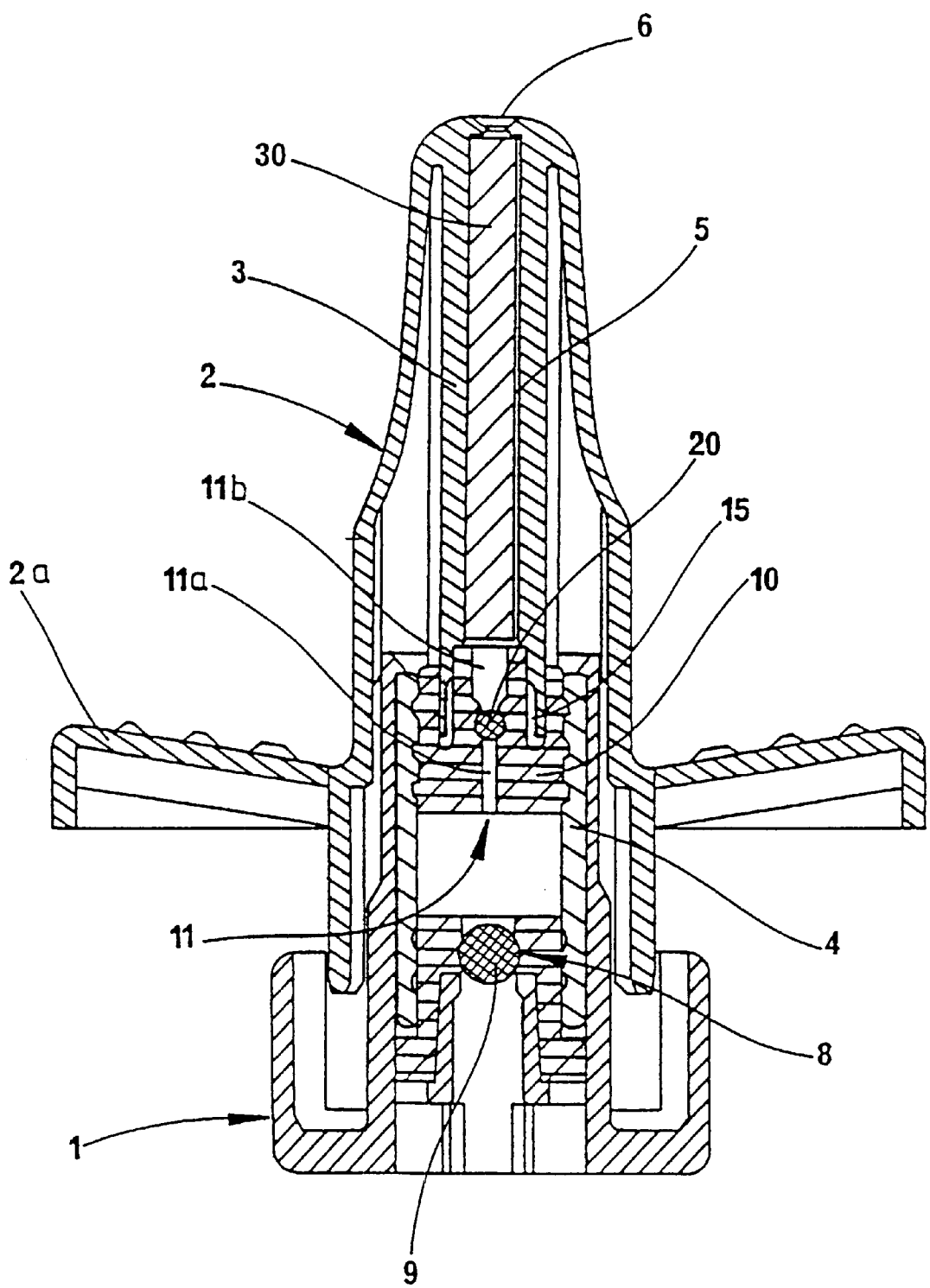
FIG. 1 is a diagrammatic front view in longitudinal section of a first embodiment of the device, which is not covered by the invention, in its storage position.
Figure 2:
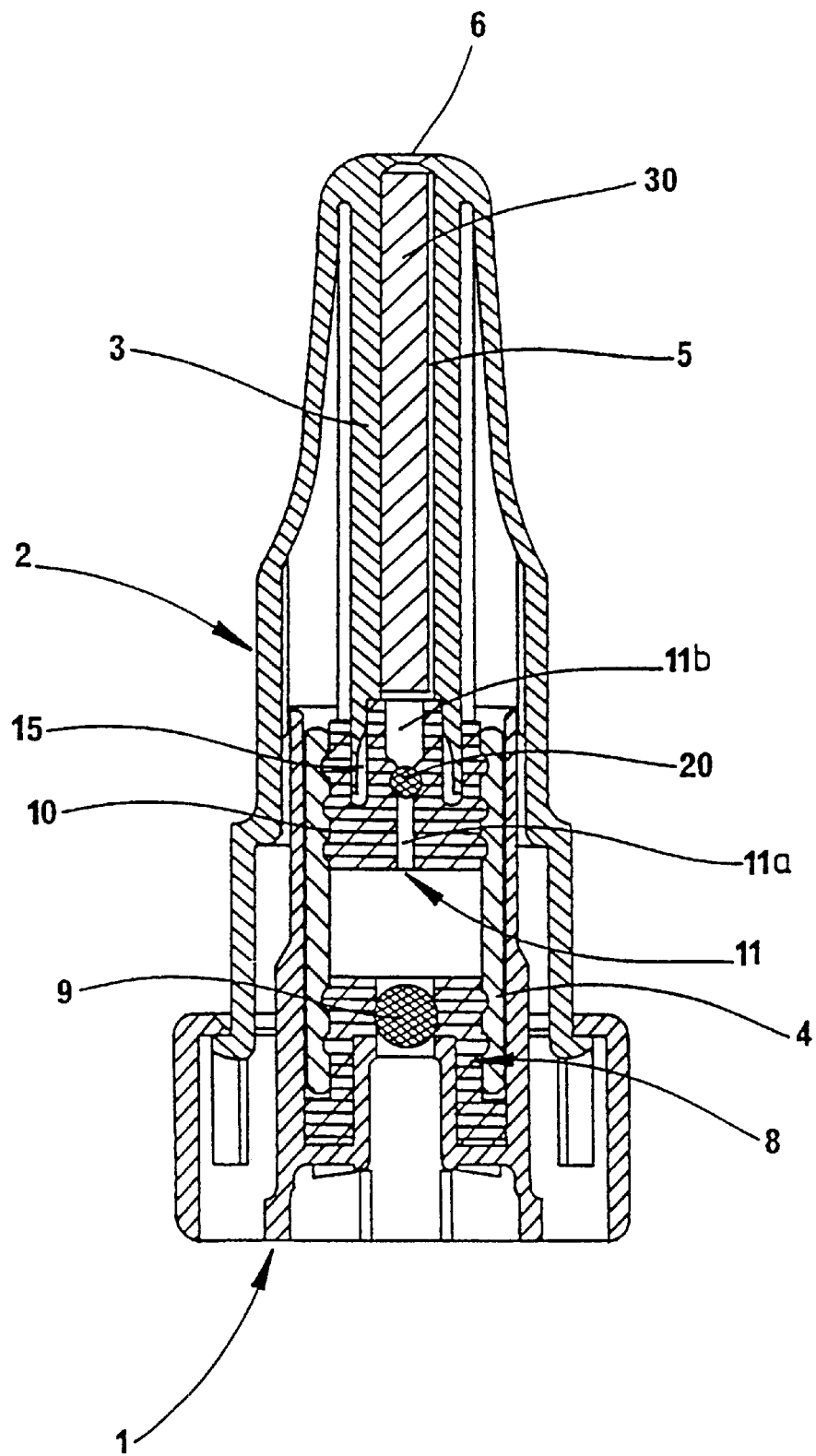
FIG. 2 is a diagrammatic side view in longitudinal section of the device of FIG. 1, in its storage position.

In the storage position, shown in FIGS. 1, 2, and 4, the cylinder therefore contains a dose of liquid and is closed firstly by the sealing stopper 8, and secondly by said piston 10, also in sealed manner. Thus, during the storage period, the liquid contained in the cylinder 4 cannot be oxidized or polluted by the outside air. In the storage position, communication between the cylinder 4 and the outlet passage 5 is therefore cut off by the piston 10.

According to the invention, the piston 10 includes a through-passage 11 which connects the cylinder 4 to the outlet passage 5. In the storage position of the piston 10, the through-passage 11 is closed in sealed manner by a closure member 20. The closure member is designed to open said through-passage 11 under the effect of a predetermined pressure which is created inside the cylinder 4 when the device is actuated, so as to enable said dose of liquid to be expelled through said through-passage 11, and then through said outlet passage 5 in the direction of the outlet orifice 6. Said through-passage 11 preferably extends axially, substantially in the middle of said piston 10 and is, at least in part, approximately cylindrical in shape. The closure member 20 is advantageously movable between a closed position in which it is disposed inside a first portion 11a of said through-passage 11, and an open position in which it is expelled out from said first portion 11a of said through-passage 11, under the effect of said predetermined pressure appearing inside the cylinder 4.

The through-passage 11 advantageously includes two portions 11a and 11b. The first portion 11a receives the closure member in its closed position, and the second portion 11b receives it in its open position. In this case, the cross section of the second portion 11b is greater than the outside dimensions of the closure member 20 in order to enable the liquid to flow through the through-passage 11 when the closure member 20 is in its open position. In addition, the closure member 20 has outside dimensions slightly greater than the cross section of the first portion 11a of the through-passage 11, so that said closure member 20 can be blocked in its closed position. As can be seen in FIGS. 3 and 5, the through-passage 11 can advantageously include a cavity 12 designed to receive said closure member 20. The cavity 12 is advantageously of shape identical to that of the closure member 20 and is designed to hold it in sealed manner in its closed position. This implementation enables the closure member 20 to be positioned in the through-passage 11 when the device is assembled, and enables the predetermined pressure required to expel said closure member 20 to be determined with greater accuracy.

After the device has been actuated, as shown in FIGS. 3 and 5, the closure member 20 is in said second portion 11b of the through-passage 11, and said through-passage 11 is no longer closed and connects the inside of the cylinder 4 to the outlet passage 5 to enable the liquid to be expelled. In its open position, the closure member 20 could possibly be found completely outside the through-passage 11 of the piston 10. In which case, the through-passage 11 is not necessarily made with two portions 11a and 11b of different cross sections.

When the user actuates the device, pressure is exerted in order to displace the bottom portion 1 of the device relative to the top portion 2 of the device. Since the liquid contained in the cylinder 4 is incompressible, said pressure is therefore transmitted directly by said liquid to the closure member 20 which is disposed in the through-passage 11. When the pressure reaches a sufficiently high predetermined level, the closure member 20 is expelled out from said first portion 11a of the through-passage 11 and the liquid contained in the cylinder is expelled through said through-passage towards the outlet passage 5, and thus the outlet orifice 6 of the device. The walls of the piston 10 which form the through-passage 11 are advantageously deformable to enable said closure member 20 to be expelled under the effect of the pressure. Thus, with reference to the figures, a radial space 15 can be provided which is disposed around said walls which form the through-passage 11 of the piston 10, so that the walls of the piston 10 can deform radially towards said space 15 to enable the closure member 20 to be expelled out from the through-passage 11.

According to the invention, the piston 10 is advantageously fixed relative to the actuator member 3 and is displaced in the cylinder 4 together with said actuator member 3 when the device is actuated. The manufacture and assembly of the dispenser of the invention is therefore greatly simplified, which leads to a substantial reduction in cost.

FIGS. 1 to 3 show a first embodiment, which is not covered by the invention, where the closure member 20 is made in the form of a ball-bearing which is inserted in the through-passage 11.

FIGS. 4 and 5 show a preferred embodiment of the invention where the closure member 20 is secured to the spray nozzle 30. In this case, the spray nozzle 30 is movable between an initial position, shown in FIG. 4, corresponding to the closed position of the closure member 20, and a final position, shown in FIG. 5, corresponding to the open position of the closure member 20. This implementation enables the device to be made using one component part fewer, thereby further benefitting manufacture and assembly of said device, and resulting in manufacturing and assembly costs being reduced. As shown in FIG. 4, said closure member 20 can advantageously be formed by a portion, e.g. a spherical portion, of the spray nozzle 30, having outside dimensions which are greater than the inside dimensions of the first portion 11a of the through-passage 11. The spherical portion 20 is connected to the spray nozzle 30 via a rod portion of suitable size, i.e. which completely occupies the empty space in the initial position of FIG. 4, and which enables the liquid to pass through when the device is actuated. In an advantageous variant, the spray nozzle 30 can also include an end portion 31 which extends into the cylinder 4 when the spray nozzle 30 is in its initial position, as shown in FIG. 4. The end portion 31 is designed to occupy, at least in part, the empty space created in the through-passage 11 when the spray nozzle 30 is in its final position shown in FIG. 5. This enables the dose of liquid contained in the cylinder 4 to be expelled totally and completely.

Thus, when the user actuates the device, pressure is created inside the cylinder which, since the liquid is incompressible, is transmitted to the spherical portion 20 of the spray nozzle 30 which forms the closure member, and which is advantageously held in said cavity 12 in said through-passage 11. When said pressure reaches a sufficiently high predetermined level, said spherical portion 20 is expelled out from the cavity 12 and the entire spray nozzle 30 is thus displaced from its initial position to its final position in which it guarantees good spraying of the dose of liquid.

The invention therefore enables a dispenser device for dispensing a single dose of liquid to be made simply and cheaply. Said dispenser device can be referred to as a single-shot spray. In particular, the device of the invention guarantees total and complete expulsion of the dose of liquid contained in the cylinder 4 because of the precompression that it generates. Thus, when the user actuates the device, a certain amount of energy is stored in the hand until a pressure is reached that is high enough to expel the closure member out from the through-passage of the piston. When the closure member is expelled out from the through-passage, the energy stored in the hand of the user results in the piston sliding suddenly and quickly in the cylinder from its storage position to its actuated position, so that the liquid contained in the cylinder is completely expelled.

The invention has been described with reference to a plurality of embodiments. Naturally it encompasses all possible combinations of the various embodiments.

What is claimed is:

1. A dispenser device for dispensing a single dose of liquid, said device comprising:

a cylinder (4) containing said dose of liquid;

a piston (10) which slides in sealed manner in said cylinder (4) between a storage position in which it isolates said cylinder and an actuated position;

a piston actuator member (3);

an outlet passage (5) for connecting said cylinder (4) to an outlet orifice (6); and a e (30) which is disposed in the outlet passage (5) for spraying the dose of liquid;

said piston (10) including a through-passage (11) which is closed in sealed manner in the storage position of the piston (10) by a closure member (20), said closure member being designed to open said through-passage (11) under the effect of a predetermined pressure which is created inside the cylinder (4), so as to enable said dose of liquid to be expelled through said through-passage (11), the device being characterized in that said closure member (20) is secured to said spray nozzle (30), said spray nozzle (30) being movable between an initial position corresponding to the closed position of the closure member (20), and a final position corresponding to the open position of the closure member (20).

2. A device according to claim 1, in which said closure member (20) is movable between a closed position, in which it is disposed in a first portion (11a) of said through-passage (11), and an open position, in which it is expelled out from said first portion (11a) of the through-passage (11).

3. A device according to claim 2, in which said through-passage (11) is at least partially cylindrical, and said closure member (20) has outside dimensions that are greater than the cross section of said first portion (11a) of the through-passage (11) so that it is blocked in the closed position, said closure member (20) being expelled out from said first portion (11a) of the through-passage (11) under the effect of said sufficient pressure which is created in the cylinder (4).

4. A device according to claim 2, in which said through-passage (11) includes a cavity (12) designed to receive said closure member (20) in its closed position.

5. A device according to claim 2, in which the walls which form the through-passage (11) of the piston (10) are deformable under the effect of a pressure that is sufficient to enable said closure member (20) to be expelled.

6. A device according to claim 1, in which the spray nozzle (30) includes an end portion (31) which extends into said cylinder (4) when the spray nozzle (30) is in its initial position, said end portion (31) being designed to occupy, at least in part, the empty space created in the through-passage (11) when the spray nozzle (30) is in its final position.

7. A device according to claim 1, in which said through-passage (11) includes a substantially cylindrical first portion (11a) and a substantially cylindrical second portion (11b), the cross section of said second portion (11b) being greater than that of said first portion (11a), said closure member (20)

having outside dimensions which are greater than said cross section of the first portion (11*a*) and which are less than said cross section of the second portion (11*b*).

8. A device according to claim 1, in which said cylinder (4) is made of glass.

9. A device according to claim 1, in which said piston (10) is fixed relative to said actuator member (3) and is displaced in the cylinder (4) together with said actuator member (3).

* * * * *